US007799008B2

(12) United States Patent
Hendricks

(10) Patent No.: US 7,799,008 B2
(45) Date of Patent: Sep. 21, 2010

(54) BOTTLE FOR DELIVERING NUTRIENTS TO AN ENTERAL FEEDING TUBE

(76) Inventor: William Hendricks, 6849 W. Avery Cir., Highland, UT (US) 84003

( * ) Notice: Subject to any disclaimer, the term of this patent is extended or adjusted under 35 U.S.C. 154(b) by 0 days.

(21) Appl. No.: 11/683,339

(22) Filed: Mar. 7, 2007

(65) Prior Publication Data

US 2008/0103475 A1 May 1, 2008

Related U.S. Application Data

(60) Provisional application No. 60/780,662, filed on Mar. 9, 2006.

(51) Int. Cl.
*A61B 19/00* (2006.01)

(52) U.S. Cl. ....................... 604/403; 604/408; 604/409; 604/410; 604/411; 206/219; 206/484; 383/107; 383/109

(58) Field of Classification Search ................. 604/403, 604/408–411
See application file for complete search history.

(56) References Cited

U.S. PATENT DOCUMENTS

| | | | | |
|---|---|---|---|---|
| 2,035,404 | A * | 3/1936 | Quinn | 215/384 |
| 2,525,745 | A | 10/1950 | Wycoff | |
| 3,153,415 | A | 10/1964 | Sheridan | |
| 3,635,367 | A | 1/1972 | Morita et al. | |
| 3,645,262 | A | 2/1972 | Harrigan | |
| 3,731,849 | A * | 5/1973 | Burrows | 222/153.06 |
| 3,744,658 | A | 7/1973 | Fujio | |
| 3,990,597 | A | 11/1976 | Barton | |
| 4,045,070 | A * | 8/1977 | Geisinger | 294/31.2 |
| 4,282,980 | A | 8/1981 | Winchell | |
| D268,722 | S | 4/1983 | Bova | |
| 4,713,064 | A | 12/1987 | Bruno et al. | |
| 4,784,641 | A | 11/1988 | White | |
| 4,976,707 | A * | 12/1990 | Bodicky et al. | 604/408 |
| 4,994,076 | A | 2/1991 | Guss | |
| 5,267,983 | A | 12/1993 | Oilschlager et al. | |
| 5,462,194 | A * | 10/1995 | Barnwell | 220/709 |
| 5,741,243 | A * | 4/1998 | Geckle et al. | 604/890.1 |
| 5,776,117 | A | 7/1998 | Haselhorst et al. | |
| 5,807,333 | A * | 9/1998 | Osborne et al. | 604/131 |
| 6,732,888 | B1 * | 5/2004 | Smiley et al. | 222/485 |
| 2003/0073971 | A1 | 4/2003 | Saker | |
| 2004/0011760 | A1 | 1/2004 | Schupp et al. | |
| 2004/0116891 | A1 | 6/2004 | Curutcharry | |

* cited by examiner

*Primary Examiner*—Tatyana Zalukaeva
*Assistant Examiner*—Ilya Y Treyger
(74) *Attorney, Agent, or Firm*—Workman Nydegger

(57) ABSTRACT

An enteral feeding device, includes a system for delivering liquid nutrients to an enteral feeding tube. The device includes: (a) a container, having first, second and third openings; (b) a tip configured to be coupled to the container, the tip having an opening in fluid communication with the first opening of the container, the second opening of the container configured such that nutrient can be delivered to the second opening and the third opening configured to receive nutrient or to allow gas expelled from the patient (e.g., through burping) to flow there through.

23 Claims, 6 Drawing Sheets

BOTTLE FOR DELIVERING NUTRIENTS TO AN ENTERAL FEEDING TUBE

CROSS-REFERENCE TO RELATED APPLICATIONS

This non-provisional patent application claims priority to and the benefit of a provisional patent application entitled, "BOTTLE FOR DELIVERING NUTRIENTS TO AN ENTERAL FEEDING TUBE," application Ser. No. 60/780,662 filed Mar. 9, 2006 to William Hendricks, which is incorporated herein in its entirety by reference.

FIELD OF THE INVENTION

This invention is in the field of containers and methods for delivering liquid nutrients to a feeding tube such as an enteral feed tube using gravity to regulate the pressure and flow of the liquid nutrients.

BACKGROUND OF THE INVENTION

When a person is unable to eat normally, it is necessary to provide other ways to provide nutrition. One treatment, among medical professionals is via enteral feeding tubes. A variety of different approaches have been developed. A few examples include percutaneous endoscopic gastrostomy (PEG), Gastrostomy tubes (G-Tube), and nasogastric tubes (NG-Tube). Many of these methods start out or end up in different places in the patient's digestive tract; however almost all of them are compatible to attach to catheter tipped syringes or equivalents, which deliver the food supply.

A variety of different methods have been developed to deliver food to these tubes. These methods are generally grouped into two groups: Gravity feeding and Mechanical pump. Another method is commonly called a Murphy drip. In this method, a mechanical pump is used to deliver fluid food to an open, vented container, which is typically a 50 cc syringe. The fluid then flows by gravity at a controlled rate into the stomach.

A variety of methods are used to deliver food to a feeding tube via gravity. One method is to use the barrel of a catheter tipped 50 cc syringe. The tip of the syringe barrel is connected to the feeding tube and food is poured into the opening that would normally fit the plunger. In the prior art, a syringe barrel has been connected to a fixture by elastic bands such that fluid nutrient delivered to the barrel is allowed to flow via gravity from the syringe barrel into a feeding tube connected to the barrel.

This method has several problems. For example, it is prone to spilling, overflows and blockages. These same troubles exist if the syringe is fed from a mechanical pump in the Murphy drip configuration.

Another method is to use a hanging bag, which is either filled or pre-filled with food. The bag is not prone to spilling or overflows; however, this method has its own problems. For example, the bags are cumbersome to hold; they usually require an I.V. pole or other hanging apparatus for their use. They are also difficult to clean well, and usually they are only used once or for just a few feedings before being discarded. The bags tend to be expensive over time.

There is therefore a need for an improved method and apparatus to dispense food via gravity to a feeding tube, which is not prone to spilling, blockages or overflows, yet is convenient to use and cost effective. There is also a need for an apparatus, which is aesthetic and not awkward especially when a person is being fed in public.

BRIEF SUMMARY OF THE INVENTION

The present invention relates to enteral feeding devices, including a system for delivering liquid nutrients to an enteral feeding tube, comprising: (a) a container, having first, second and third openings; and (b) a tip configured to be coupled to the container, the tip having an opening in fluid communication with the first opening of the container. The second opening of the container is configured such that nutrient can be delivered to the second opening and the third opening is configured to receive nutrient or to allow gas expelled from the patient (e.g., through burping) to flow there through.

An example of an enteral feeding device of the present invention is an enteral feeding device that includes (i) an open-ended, generally cylindrical plastic container; and (ii) a cap having a hollow, tapered and stepped or barbed tip suitable for connecting to a feeding tube, such as an enteral feeding tube. The tip has an aperture which is designed with a gently sloped tapered tip so as to not be prone to blockages. A threaded interior cap portion holds the tapered tip on the end of the container. The device further includes a disk shaped gasket for sealing the cap to the container. The container has a medicine port, a feeding port, and at least one flexible plastic hanging ring suitable for hanging the device from an I.V. pole, a stand or similar apparatus.

Benefits of the invention include the following aspects. First, the container virtually eliminates spills or overflows. The entire volume of food is contained in the container. Furthermore, venting provided by opening either the medicine port and/or the feeding port allows food to flow into or out of the container, and prevents (1) a vacuum from forming within the reservoir; and (2) pressure buildup within the reservoir due to food or gas (e.g., expelled by burping) being expelled back into the container. In addition, raising or lowering the container conveniently controls the feeding rate.

Moreover, the apparatus is not prone to blockages. The design of the openings and the tip in general are less likely to clog than a syringe body would be. If blockages do occur, the additional fluid capacity of the container reservoir can make it easier to clear by closing the vents and lightly shaking the bottle. An alternate method of clearing blockages would be to close the feeding port, and eject some air into the medicine port using a small oral syringe. The slight pressurization of the container would clear the blockage.

Another advantage is the opportunity for convenient feedings. The container accepts enough food for a full feeding. Only one hand is needed to hold the bottle. If an infant is being fed, it is easier to hold the baby in a natural feeding position.

In addition, since the apparatus can be similar in appearance to a common infant feeding bottle, it is much less awkward to feed a baby in pubic. The more natural feeding position and the fact that the container can be held near the baby's mouth are additional factors in relieving the awkwardness that can accompany an enteral feeding of an infant.

The device is also convenient and effective for enteral feeding adults of all ages. The device is compatible for use with an I.V. rack and an external mechanical pump. This configuration is shown herein. This configuration is beneficial for people who are not easily able to tolerate being hooked up directly to a mechanical pump. The venting prevents pressure build up and the container provides a place for the food to accumulate, thus allowing such a person to more easily control the rate of food intake. The vent(s) also allow the gas leaving the stomach of the patient to escape.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

Figure 1:
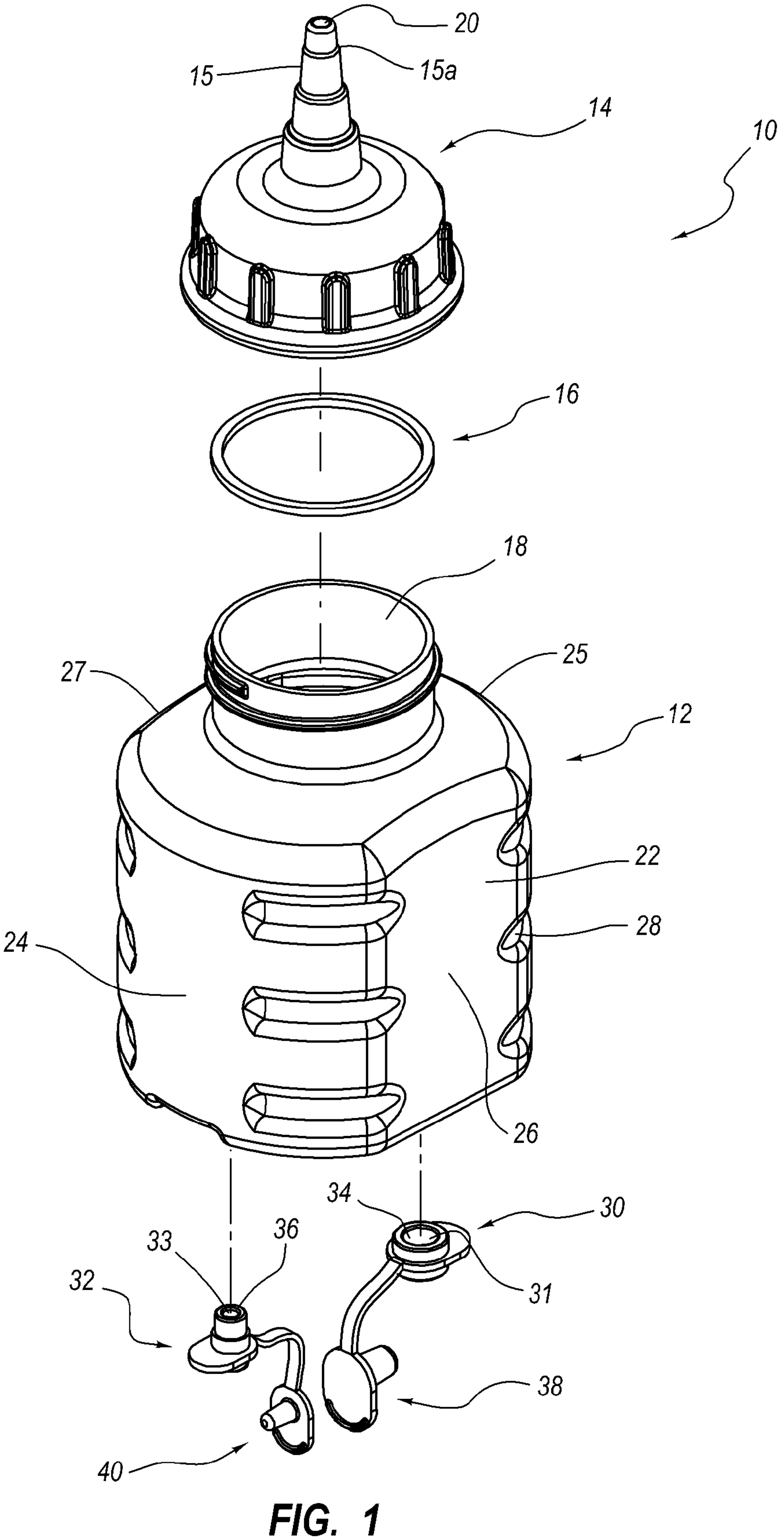
FIG. 1 shows an exploded, delivery end perspective view of one embodiment of an enteral feeding bottle of the present invention.

FIG. 1 demonstrates an exploded, perspective delivery, tip end view of a nutrient delivery system 10 of the present invention. System 10 is a bottle comprised of a container 12, a cap 14 having a tip 15, and a gasket 16 conveniently disposed between container 12 and cap 14 for sealing purposes. Container 12 has a first opening 18 that is in fluid communication with an opening 20 in tip 15 when cap 14 is coupled to container 12 (e.g., selectively, threadedly coupled), thereby enabling fluid nutrients to be delivered from container body 22 through opening 20 into a feeding tube, such as an enteral or gastric feeding tube or other device or opening.

As shown in FIG. 1, container 12 comprises hollow body 22 which has first and second curved walls 24, 25 on opposing sides thereof for convenient gripping, and at least one, and preferably first and second substantially flat walls 26, 27 for convenient gripping and for conveniently laying system 10 on its side. A plurality of grooves 28 are also present in hollow body 22 for convenient gripping and finger placement.

Figure 7:
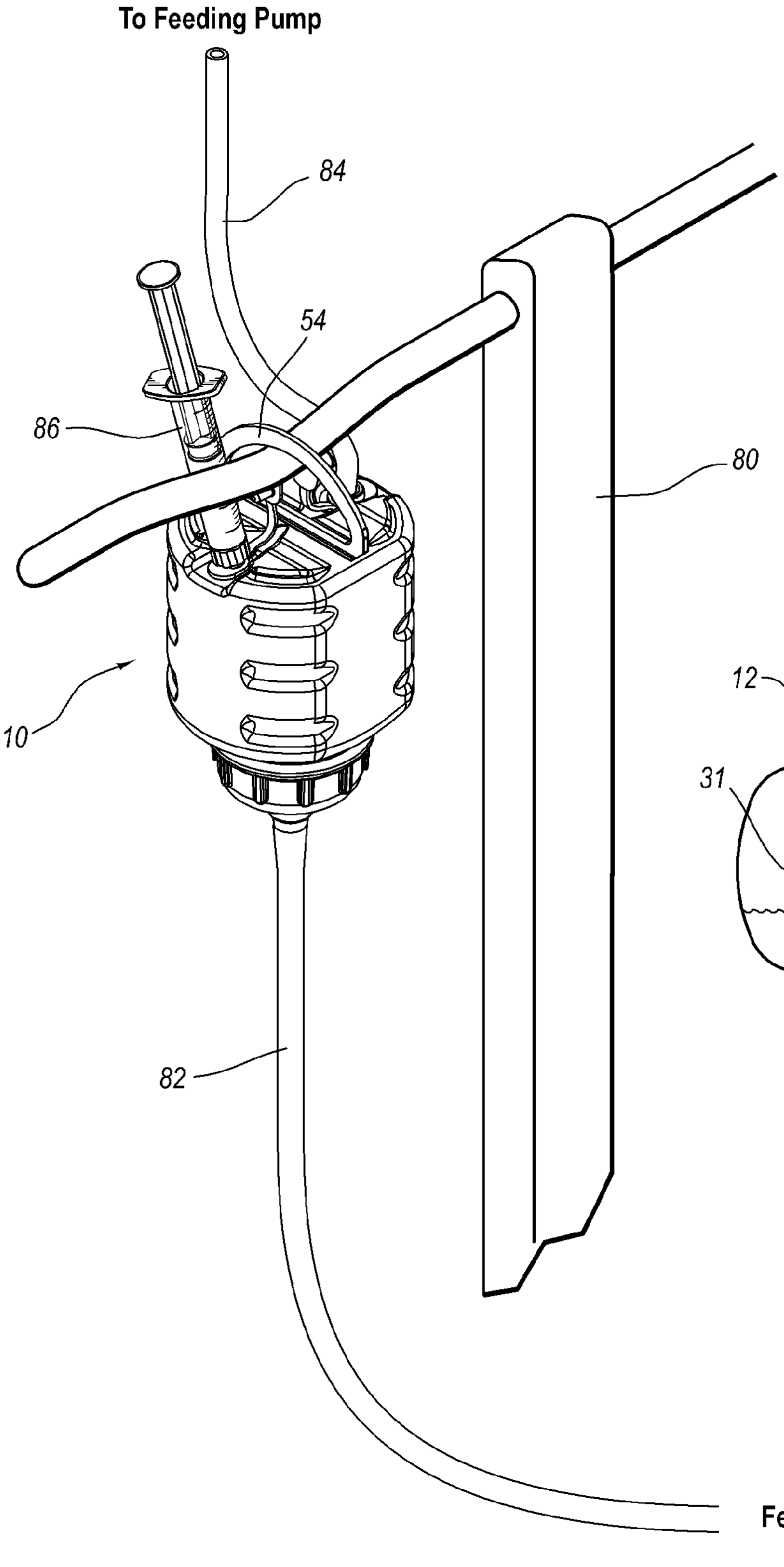
FIG. 7 demonstrates the bottle of FIG. 1 in a Murphy drip configuration connected to an I.V. pole wherein (i) a syringe is used to add medicine through one port, (ii) a tube is connected to another port and to a feeding pump to thereby deliver fluid nutrient to the bottle, and (iii) and the tip of the bottle is connected in fluid communication with a feeding tube to deliver fluid nutrient via gravity to the feeding tube for feeding a patient.

Container 12 is configured to be coupled in fluid communication with a feeding tube (see FIG. 7). Cap 14 configured to be coupled to container 12. Cap 14 has a tip 15 having an opening 20 configured to be in fluid communication with first opening 18. Tip 15 is configured to couple container 12 in fluid communication with a feeding tube (as shown in FIG. 7) such that fluid delivered to container 12 flows through tip 15 into the feeding tube.

With continued reference to FIG. 1, the stepped or barbed tip 15 of cap 14 shown in FIG. 1 is designed to securely mate to a feeding port end of a feeding tube, such as a commonly used gastro intestinal feeding tube. Tip 15 may be similar in profile to a large catheter tipped syringe, however it has a plurality of steps 15*a* in the exterior surface thereof it to make it more versatile, such that it can be connected to tubes having a variety of different diameters. Tip 15 may also (or alternatively) have barbs therein to facilitate an even stronger connection to a feeding tube.

It is often beneficial to have a better connection to the feeding tube. If the tube becomes separated from a feeding source during feeding, food and perhaps medicine will be lost. In one embodiment, the connection is not designed to be permanent, however, as it can be useful to be able to separate the tip from the feeding tube for cleaning purposes. Thus a stepped or barbed tip such as tip 15 is a highly useful development.

The aperture 20 at the small end of the tip 15 is in one embodiment, wider than the typical tip of a catheter tipped 50 cc syringe and narrow enough to still allow the outer shell to have a convenient fitting into an enteral tube. In one embodiment, the internal surfaces are smooth, and generously tapered so as to be less prone to blockages.

Cap 14 is selectively, threadedly coupled to container 12. Alternatively, however, a cap of the present invention having a hollow delivery tip can be integrally coupled to a hollow container to form a bottle of the present invention.

Figure 2:
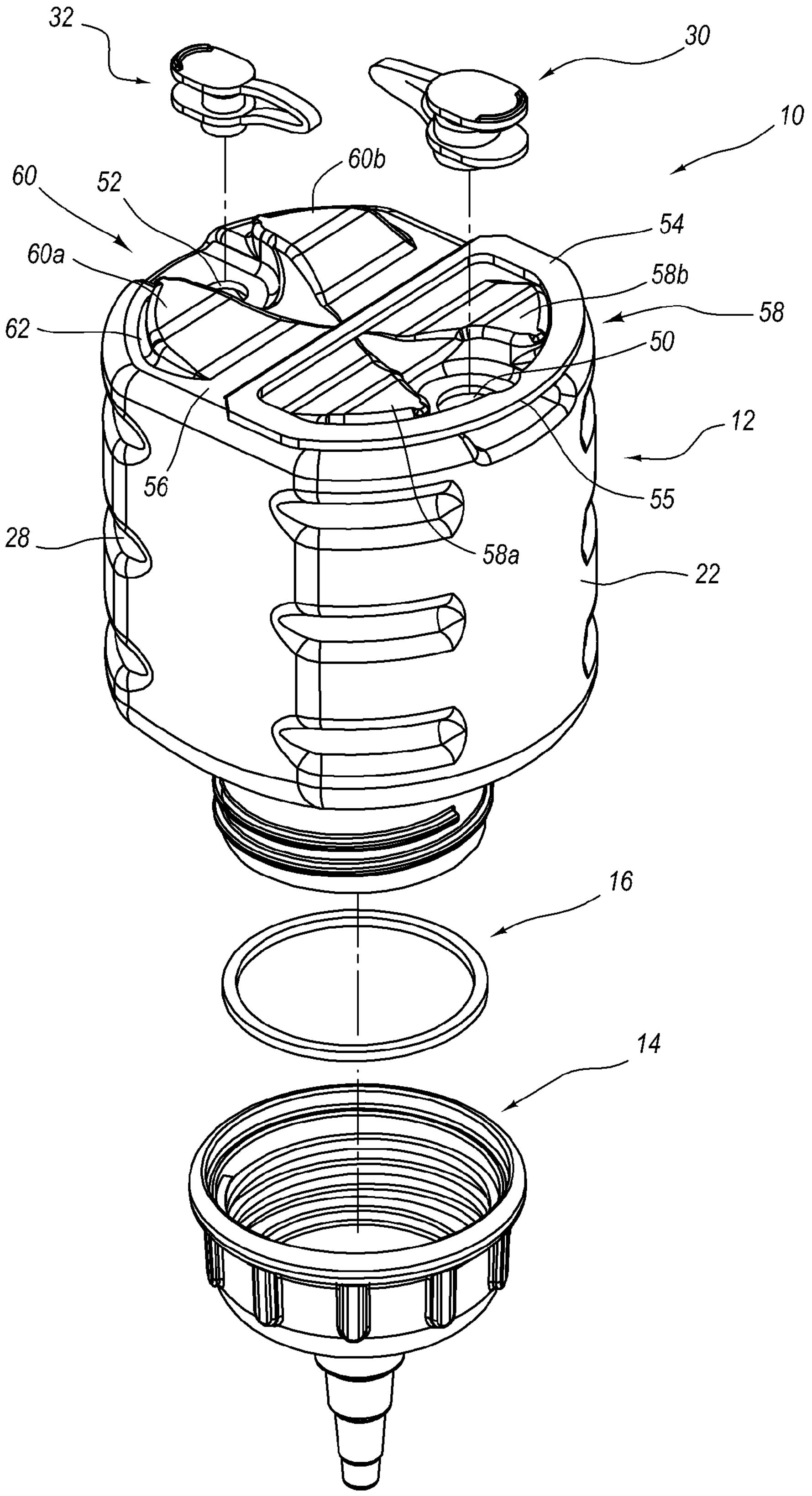
FIG. 2 shows an exploded, receiving end perspective view of the bottle of FIG. 1.

The vented, receiving end of system 10, through which nutrient can be received during use, is further illustrated in FIG. 2. With reference to FIGS. 1 and 2, container 12 further comprises first and second ports 30, 32 coupled to container body 22. Ports 30, 32 have respective openings 31, 33 therethrough. Ports 30, 32 have hollow port bodies 34, 36 respectively, and port caps 38, 40 respectively tethered thereto. Ports 30, 32 may be integral with container body 22 or may be manufactured separately therefrom, then coupled to body 22, for example, for ease of manufacturing.

Port bodies 34, 36 define openings 31, 33 therethrough, said openings enabling fluid nutrient and/or medicament to be delivered to container 12 and/or provide one or more openings for expelled gas from burping or other functions to be dispelled therethrough and in order to prevent a vacuum from occurring within container 12.

As illustrated in FIG. 1, first opening 18 is located in the delivery end of container 12. Openings 31, 33 are examples of second and third openings, respectively, of container 12, and are located in the opposing, receiving end of container 12, as shown in FIG. 2.

With continued reference to FIG. 2, container body 22 has first and second openings 50, 52 into which hollow port bodies 34, 36 of respective ports 30, 32 are inserted for convenient manufacturing. Optionally, hollow ports 30, 32 are integrally connected to container body 22 and are formed integrally thereon during the manufacturing process. Thus, container 12 has first and second selectively closeable openings 31, 33 in the receiving end thereof for venting and/or infusion of liquids such as nutrients and medicine. The openings of a container of the present invention may be defined by ports 30, 32 that are connected to body 22 or by simple holes made in the container body 22.

A hanging loop 54 (e.g., for hanging on an I.V. pole) is flexibly coupled to a receiving end surface 56 of container body 22 so as to be moveable with respect to receiving end surface 56. Receiving end surface 56 of container body 22 has a first raised protrusion region 58 having raised portions 58A, 58B and a second raised protrusion region 60 having raised portions 60A, 60B adjacent which loop 54 is conveniently placed when not in use. Moveable loop 54 can be selectively moved between region 58 and 60 so as to be placed in a storage position adjacent region 58 or 60. FIG. 2 demonstrates the storage position adjacent region 58.

Extending about each of the raised regions 58, 60 is a respective groove 63, 62 (FIG. 3) into which loop 54 selectively moves (e.g., snaps) in order to move loop 54 into a desired storage position, as shown in FIG. 2. Loop 54 is thus movable from one groove 62, 63 to another, or can be moved to a position therebetween for hanging from a pole. Loop 54 is located in the center of the receiving end surface 56 of body 22 of container 12 for balance. As shown in FIG. 2, hanging loop 54 closes substantially flush with an outer rim of the container 12 for efficient use of space.

Figure 3:
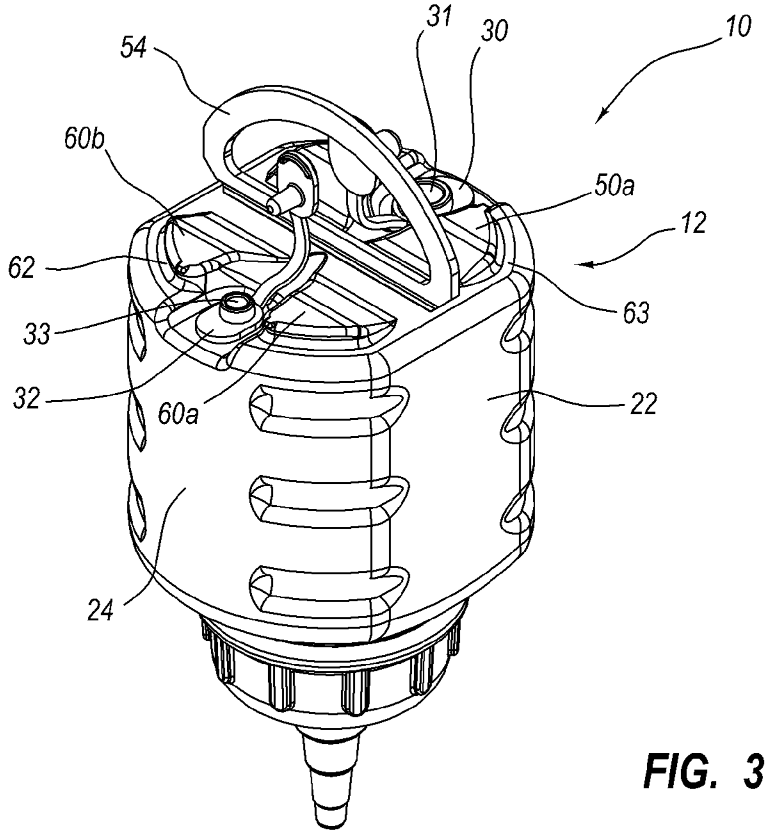
FIG. 3 is a receiving end perspective view of the bottle of FIG. 1.
Figure 4:
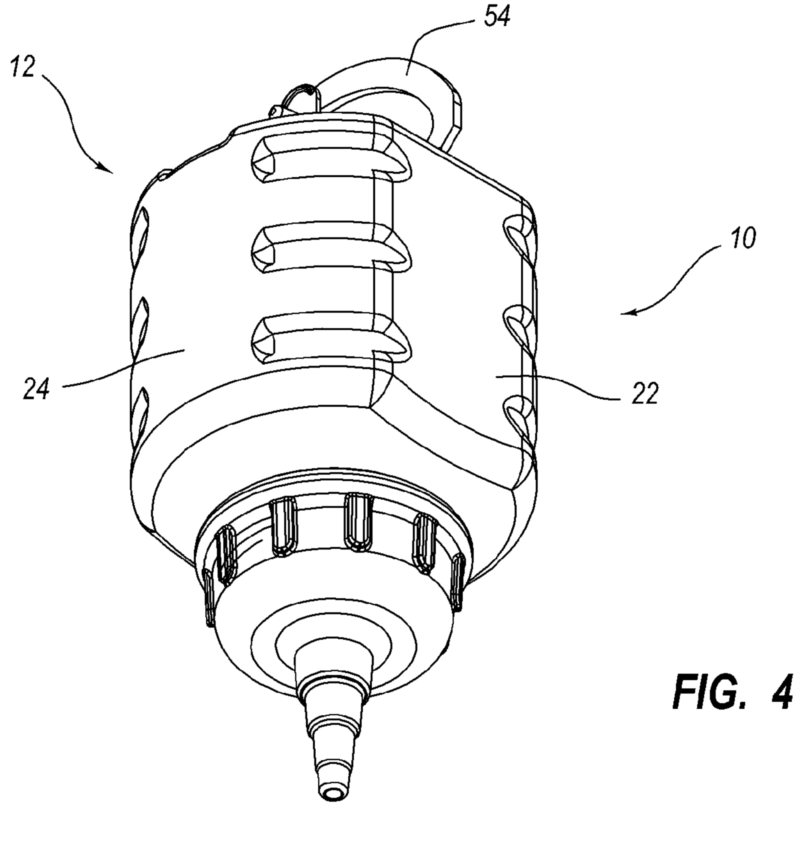
FIG. 4 is another a perspective view of the bottle of FIG. 1 illustrating the tip thereof

Turning now to FIG. 3, system 10 is shown in an assembled view with loop 52 shown in a use position, e.g., to be connected to an I.V. pole, or other member, and with ports 30, 32 being shown mounted onto container body 22 in an open position such that fluid and/or gas can be infused into or out of container 12. FIG. 3 shows ports 30, 32 with the port caps in an open position such that nutrients and/or medicament can be fed through one or more ports 30, 32. Caps 38, 40 (FIG. 1) serve as covers for the respective second and third openings 31, 33 of container 12. By providing two ports, 30, 32 one port can serve to receive nutrients, while the other port can serve as a medicine port or as a means for preventing a vacuum from forming within container 12. As further illustrated in FIG. 3, hanging loop 54 can be conveniently placed into groove 62 or groove 63 such that loop 54 is conveniently stored as illustrated in FIG. 2. As further shown in FIG. 3, the corresponding raised regions 58*a-b* and 60*a-b* enable the loops 54 to be placed in a respective corresponding groove 62, 63 such that loop 54 is conveniently stored flush with a rim of container 12.

The hanging loop(s) and ports are generally designed such that they can be tucked inside body 22 of container 12. This will allow the container 12 to be rested on a level surface without tipping over, when desired, but when the hanging loop(s) is opened, container 12 can be securely hung from an I.V. pole or similar device.

As reflected in FIG. 3, the medicine/vent port shown as item 32 would typically be open with the cap unplugged during feeding. This would allow a vent so that liquid food and or gas, such as air, could enter and leave the reservoir without pressure buildup. In one embodiment, the medicine port 32 would be sized to seal to a typical oral syringe (as shown in FIG. 7). This would facilitate the addition of medicines, which are compatible to be given with food. It would also facilitate the addition of rinse water to be added after the feeding, and/or a slight pressurization of air to clear any blockages.

Figure 5:
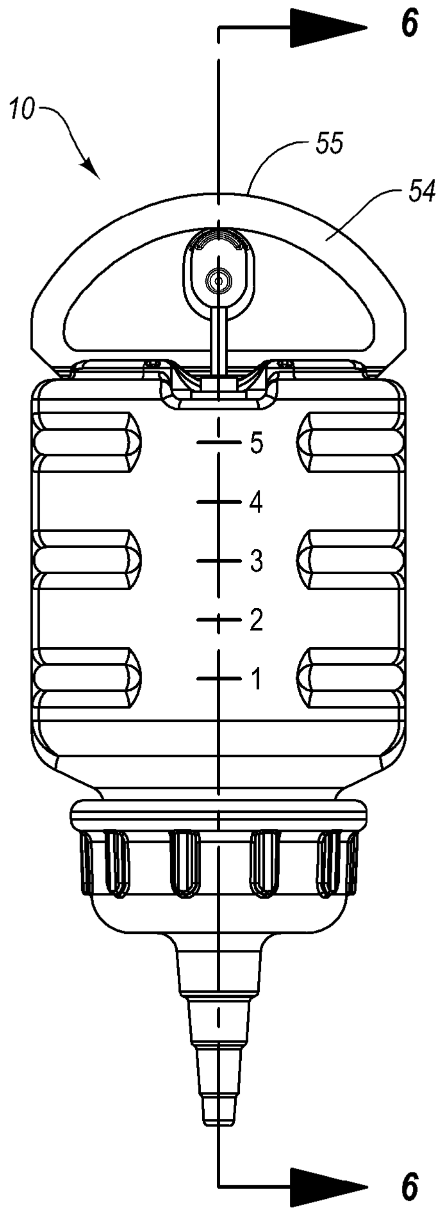
FIG. 5 is a side perspective view of the bottle of FIG. 1 with the delivery, tip end pointing downward.
Figure 6:
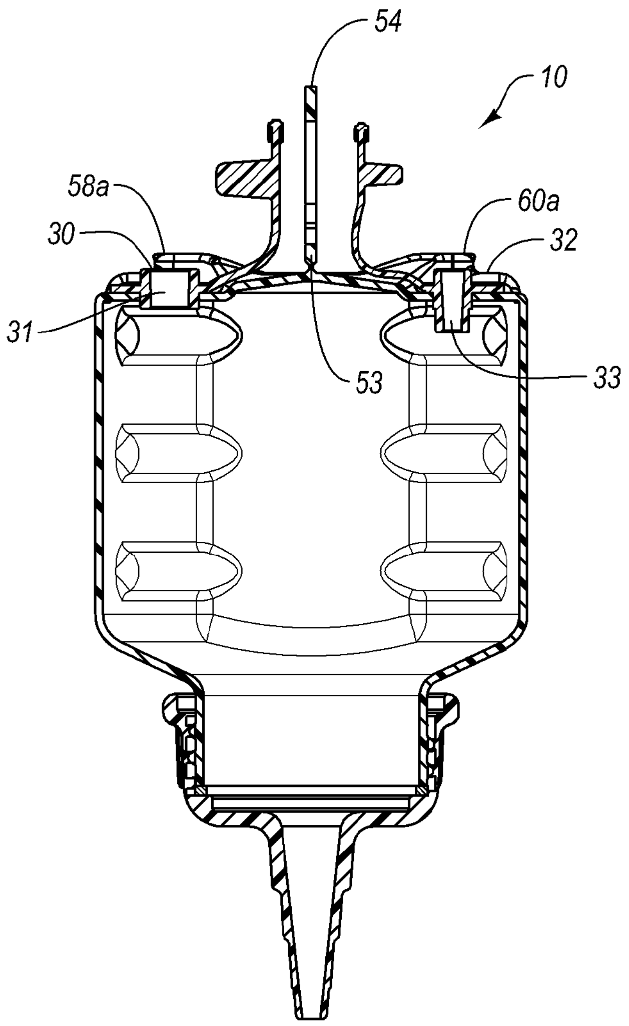
FIG. 6 is a cross-sectional view of the bottle shown in FIG. 5.

With reference now to FIGS. 5 and 6, loop 54 is further shown in the operable position. As illustrated, loop 54 can be moved to either side in order to be stored conveniently, thus convenient access is enabled at all times to either of ports 30 or 32. It is also illustrated that protuberances 60A-B and 58A-B are conveniently placed so that loop 54 can be conveniently moved to one side or to the other as desired by the user. Thus, system 10 further comprises at least one protuberance on the container, the protuberance being configured such that the hanging loop 54 can be placed adjacent to the protuberance and fit into a groove defined by the at least one protuberance and the body 22 of the container 12 such that the hanging loop 54 is selectively, conveniently stored flush adjacent the container body 22.

With continued reference to FIGS. 2 and 5-6, as well as the additional figures herein, the location of the openings 31, 33 is synchronized with the location of loop 54 such that the base 53 of loop 54 is connected to connector body 22 between the second and third openings 31, 33 and such that when the upper portion 55 of loop is folded over selected protuberances (58A-B or 60A-B), the upper portion 55 of loop folds over one or the other opening 31, 33, such that each opening 31, 33 can be conveniently accessed even when the loop is in the storage position.

Figure 8:
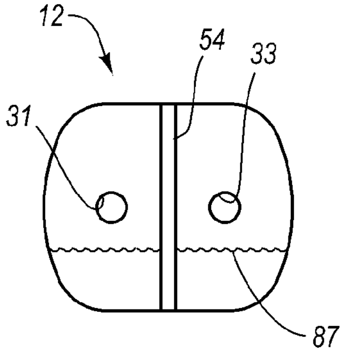
FIG. 8 is a schematic view illustrating the receiving end surface of the bottle of FIG. 1, demonstrating that the opposing ports are above the level of liquid located therein when the bottle is positioned on a flat side thereof to thereby prevent liquid from leaking out of the bottle.

As further shown, the opening 31, 33 of each respective port 30, 32 is located between first and second respective protuberances 58*a*, 58*b* or 60*a*, 60*b* such that the hanging loop 54 can be folded over the protuberances while still allowing accessibility to the port holes. Thus, the second and third openings 31, 33 are mounted at polar opposite sides of the receiving end surface of container 12 such that the container 12 can be placed on a side without the openings being adjacent to the support surface such that liquid will not spill out of the second and third openings. This dynamic is illustrated in FIG. 8, which shows a schematic drawing illustrating the concept of the openings being above the fluid level 87 of fluid nutrient when container 12 is laid on its side. As illustrated, regardless of which flat size container 12 is laid on, fluid level 87 will not reach openings 31, 33, such that a less than full bottle system 10 can be laid on its side for convenient feeding (e.g., when not hung from a pole) if desired.

As further shown in FIG. 5, a scale having indicia such as numbers 1-5, or other indicia as desired, is imprinted on container 12, as shown in FIG. 5, indicating the fluid volume contained or yet to be dispensed. There may also be printing patterns that would be reminiscent of those shown on many infant feeding bottles. The intent of the printing would be to enhance the aesthetic look of container 12 and to make it convenient, e.g., for parents to use the system while feeding their small children in public. Other embodiments may include larger reservoirs with printed designs or designs suitable for adults. In one embodiment, gradient markings, such as shown in FIG. 5, are displayed in a first sequence on one side and then the opposite sequence on another side. Thus, whatever direction the container is tipped, the gradient marking display the amount of fluid enclosed in the container.

FIG. 7 demonstrates that system 10 can be conveniently hung from a desired location with loop 54 in the operable position. Loop 54 is shown conveniently hanging from an I.V. pole 80 with loop 54 being shown in an operational position, such that system 10 can be conveniently connected to a patient feeding tube 82 leading to a patient, e.g., the stomach or nasogastric tube of a patient to thereby conveniently deliver nutrient to feeding tube 82 via gravity. Container 12 is in fluid communication with a feeding pump via tube 84. Tube 84 can lead to port 30 or 32.

In one embodiment, the opening of one port is larger than the opening of another port. This may help to distinguish which tube should be placed in a certain location or to be compatible with different sized delivery devices, for example. For example, opening 33 may be connected to a feeding pump via tube 84 while opening 31 may be connected to a syringe 86 or other delivery device for delivering fluid such as a medicine to system 10. Optionally one or more ports can remain open without a delivery device connected thereto such that a vacuum will not form within container 10 and to provide venting during use. It is beneficial to hang container 12 for longer term feedings or feedings set up in the Murphy drip configuration shown in FIG. 7. The ports may be closed when it is desired to transport the bottle to another location.

Figure 9:
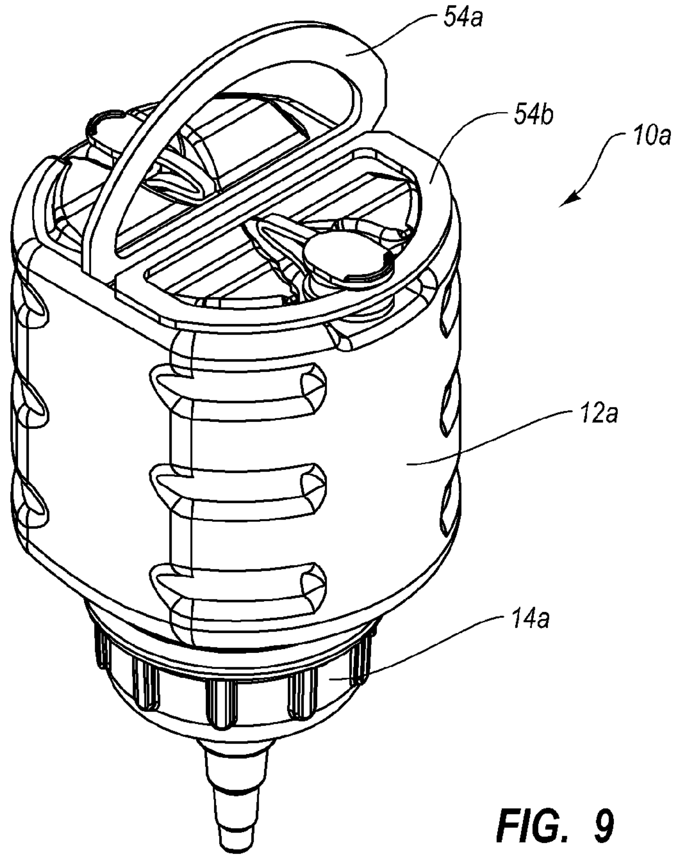
FIG. 9 is a receiving perspective view of an alternative enteral feeding bottle of the present invention having a plurality of flexible hanging loops coupled to the receiving end surface of the container.
Figure 10:
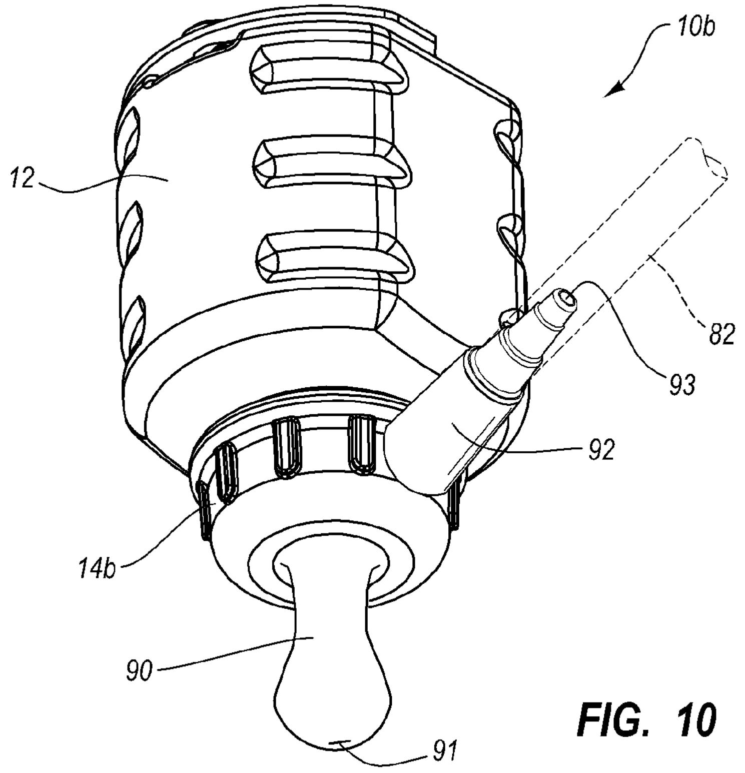
FIG. 10 is a perspective view of yet another embodiment of the bottle of the present invention comprising a cap having first and second tips that are in fluid communication with the opening of the container and that each have an opening therein such that nutrient can be delivered through the one or more of the tips such that the bottle can deliver liquid nutrients to a feeding tube and/or to the mouth of a patient such as an infant.

Alternative nutrient delivery bottles 10*a* and 10*b* are shown in FIGS. 9 and 10 respectively. As illustrated, nutrient delivery system 10*a* has exactly or substantially the same components as system 10 except that first and second movable, foldable hanging loops 54*a*, 54*b* are connected to body 12*a*. Loops 54*a*, 54*b* can be folded over respective protuberances. First and second loops 54*a-b* can be provided for structural strength (e.g., using two loops rather than one), for variety in selecting loops, for convenience in providing different loops in different locations, or for any other reason.

With respect to FIG. 10, alternative nutrient delivery system 10*b* has a cap 14*b* having multiple tips thereon identified at 90 and 92. In this embodiment it is possible for the patient such as a baby to receive nutrients from (i) a first tip, e.g., rigid hollow tip 92 that is coupled to a feeding tube 82, e.g., a gastric or enteral feeding tube feeding into the stomach; and/or (ii) from a second tip, e.g., nipple 90 which is a soft, flexible nipple that can feed into the mouth of the baby. Nipple 90 may comprise a typical flexible nipple used in a baby bottle, for example, having a hole 91 (e.g., a slit) therethrough for feeding an infant. This dual tip system provides the user the opportunity to feed the baby enterally via a feeding tube 82 in one instance and then feed via the baby's mouth in another or to give the sensation of sucking nutrient from the bottle, while simultaneously receiving fluid nutrients enterally such that the baby associates the reception of fluid nutrient with the sucking reflex.

Thus, tip 92 may be a rigid, hollow tip for connecting to a feeding tube while tip 90 is a flexible tip having a hole 91 therein for reception within the mouth of an infant for sucking purposes. FIG. 10 is thus a perspective view of bottle system lO*b* comprising a cap 14*b* having first and second tips 90, 92 that are each in fluid communication with the first opening 18 of the container 12 when cap 14*b* is coupled to container (e.g., threadedly coupled). Tips 90, 92 each have a respective opening 91, 93 therein such that nutrient can be delivered from container 12 through either one or through both of the tips 90, 92 such that the bottle 10*b* can deliver liquid nutrients to a feeding tube and/or to the mouth of a patient such as an infant. Tip 92 is a rigid hollow tip (that may be identical or similar to tip 15 for example) for connecting to a feeding tube 82 (as shown in broken phantom lines in FIG. 10) while the second tip 90 is a flexible tip having a hole 91 therein (e.g., a slit) for reception within the mouth of a patient (e.g., an infant) for sucking purposes, similar to a nipple used in a baby bottle.

The alternate embodiment shown in FIG. 10 may be useful for infants who are in a transitory state in which they are able to consume a small amount of food orally and enterally at the same time and provides the benefit of allowing the infant to associate pleasant full feelings with oral feedings. The embodiment allows the infant to be fed in both manners, i.e., orally via the infant's mouth and enterally via a feeding tube simultaneously using the same bottle system 10. Thus, the feeding through the tips 90, 92 can be successfully performed simultaneously or by feeding through one tip 90 or the other tip 92 at separate times.

A variety of different materials can be used to make the system 10. For example, in one embodiment, container 12 comprises polypropylene and gasket 16 comprises of an elastomeric seal comprising, for example, nylon or silicone. Ports 30, 32 may comprise a snap-in mounting port that comprises nylon, silicone, or some other sealable material, for example, or may be integral with container 12. In one embodiment, the larger port is designed to fit a tube for a feeding pump while the smaller port is for a syringe and for preventing a vacuum from occurring.

In addition to acting as a source of nutrients, the system 10 of the present invention also acts as an exit container, providing a receptacle for vented (e.g., burped) food or gas. Thus, use of the system 10 provides a method of receiving vented material from a stomach, for example. System 10 is thus particularly useful because of the use of second and third openings 30, 32, one of which can act to supply nutrients while the other acts as a vent.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A system for delivering liquid nutrients to a feeding tube to provide nutrients to a patient, comprising:

a rigid container having a first opening in a delivery end of the container, the container being configured to be coupled in fluid communication with a feeding tube, the container further having second and third openings in another end of the container, such that nutrient can be delivered to one of said second and third openings and the other of the second and third openings can receive fluid therethrough or can allow gas to vent therethrough; and a cap configured to be coupled to the container, the cap having a first, rigid tip configured to couple the container in fluid communication with a feeding tube, and a second, flexible tip configured in size and shape for sucking by the mouth of an infant;

wherein the second, flexible tip is substantially perpendicularly oriented with respect to the first, rigid tip to allow a user to suck on the second, flexible tip while simultaneously receiving nutrients enterally through the feeding tube that is coupled in fluid communication to the first, rigid tip.

2. A system as recited in claim 1, wherein the inner surface of the first, rigid tip is tapered and the outer surface of the first, rigid tip is tapered.

3. A system as recited in claim 1, further comprising a hanging loop coupled to the container.

4. A system as recited in claim 3, further comprising at least one protuberance on the container, the protuberance being configured such that the hanging loop can be moved adjacent to the protuberance and fit into a groove defined by the protuberance and the body of the container such that the container loop is conveniently stored adjacent the container body.

5. A system as recited in claim 4, wherein the location of the second and third openings is synchronized with the location of the loop such that the loop is connected to a body of the container between the second and third openings and such that when the loop is folded over the protuberances, the loop folds over at least one opening, such that the at least one opening can be conveniently accessed even when the loop is in the closed position.

6. A system as recited in claim 3, wherein at least one of the first and second openings is located between first and second protuberances such that the hanging loop can be folded over the first and second protuberances while still allowing accessibility to the opening.

7. A system as recited in claim 3, wherein the hanging loop is located in the center of an end of the container for providing balance to the system.

8. A system as recited in claim 3, wherein the hanging loop closes substantially flush with an outer rim of the container for efficient use of space.

9. A system as recited in claim 1, wherein the second and third openings are mounted at opposite ends of a surface of the container such that the container can be placed on a side of the container without the openings being adjacent to the support surface and such that liquid within the container will not spill out of the second and third openings.

10. A system as recited in claim 1, wherein the container further comprises a plurality of finger grooves.

11. A system as recited in claim 1, wherein the second and third openings enable a patient to vent gas or other material out of one opening while receiving fluid nutrient through another opening.

12. A system as recited in claim 1, further comprising covers for the respective second and third openings.

13. A system as recited in claim 1, wherein the container has at least one substantially flat side.

14. A system as recited in claim 1, wherein the second and third openings are located on opposite sides of a receiving end surface of the bottle from each other.

15. A system as recited in claim 1, wherein the second opening is configured to be connected to a pump such that nutrient flows into the container, while the third opening is open such that gas can be vented from the third opening.

16. A system for delivering liquid nutrients to a feeding tube via gravity to provide nutrients to a patient, comprising:

a rigid container having a first opening;

a cap configured to be coupled to the container, the cap having a first tip, the first tip having an opening configured to be in fluid communication with the first opening of the container and an end configured in to be secured to a feeding tube, the cap further having a second, flexible tip substantially perpendicularly oriented with respect to the first tip to allow a user to suck on the second, flexible tip while simultaneously receiving nutrients enterally through the feeding tube that is coupled in fluid communication to the first tip;

the container further having a receiving end surface including a first raised portion and a first recessed portion formed in a first side thereof, and a second raised portion and a second recessed portion formed in a second opposing side thereof, wherein the first recessed portion and second recessed portion respectively include second and third openings, such that nutrient can be delivered to one of said second and third openings and the other of the second and third openings can receive fluid therethrough or can allow gas to vent therethrough;

a hanging loop coupled to a body of the container such that the system can be hung from a pole to thereby provide nutrient to a patient via a gravity feed, the hanging loop being configured to be selectively moved between a first storage position, an operative hanging position, and a second storage position;

a first groove extending into the first raised portion, the first groove being configured in size and shape to have a snap fit relationship with the hanging loop whereby the first groove locks the hanging loop in the first storage position against the receiving end surface of the rigid container; and a second groove extending into the second raised portion, the second groove being configured in size and shape to have a snap fit relationship with the hanging loop whereby the second groove locks the hanging loop in the second storage position against the receiving end surface of the rigid container.

17. A system as recited in claim 16, further comprising a second hanging loop coupled to the container for aiding in conveniently hanging the container on a pole or other object.

18. A system as recited in claim 17, wherein the cap is selectively, threadedly coupled to the container.

19. A system as recited in claim 16, wherein the hanging loop extends radially beyond the second opening when in the first storage position, and the hanging loop extends radially beyond the third opening when in the second storage position, such that both the second and third openings are accessible when the hanging loop is in the first storage position, the second storage position, or the operative hanging position.

20. A system for delivering liquid nutrients to a feeding tube to provide nutrients to a patient, comprising:

a rigid container having a receiving end surface, a second end surface including a first opening, and two curved walls and two substantially flat walls extending between the receiving end surface and the second end surface, wherein a plurality of finger grooves are formed in at least the two curved walls;

wherein a first side of the receiving end surface of the rigid container includes a first protrusion region and an opposing second side of the receiving end surface includes a second protrusion region; wherein the first protrusion region at least partially surrounds and defines a first recessed portion, and the second protrusion region at least partially surrounds and defines a second recessed portion;

wherein the first protrusion region comprises a first raised portion and a second raised portion separated by the first recessed portion;

wherein the second protrusion region comprises a first raised portion and a second raised portion separated by the second recessed portion;

a cap configured to be removably coupled to the rigid container, the cap having a first tip configured to be inserted within a feeding tube, the first tip having an opening in fluid communication with the first opening of the container, a tapered inner surface, and a tapered outer surface, the cap further having a second, flexible tip extending from the cap in a direction substantially perpendicular with respect to the first tip to allow a user to suck on the second, flexible tip while simultaneously receiving nutrients enterally through the feeding tube that is coupled in fluid communication to the first tip;

the container further having a second opening formed in the first recessed portion of the receiving end surface between the first and second raised portions of the first protrusion region, and a third opening formed in the second recessed portion of the receiving end surface between the first and second raised portions of the second protrusion region, the second and third openings being selectively closeable, the second and third openings configured such that nutrient can be selectively delivered to one of said openings and the other of said openings can receive fluid therethrough or can allow gas to vent therethrough; and a hanging loop coupled to a body of the container such that the system can be hung from a pole to thereby provide nutrient to a patient via a gravity feed, the hanging loop being located in the center of the container body in order to balance the container body, the hanging loop being configured to be selectively moved between a first storage position adjacent one side of the container body, an operative hanging position, and a second storage position adjacent the other side of the container body;

wherein the first and second raised portions of the first protrusion region each comprise a first groove configured in size and shape to have a snap fit relationship with the hanging loop whereby the first groove locks the hanging loop in the first storage position against the receiving end surface of the rigid container, and the first and second raised portions of the second protrusion region each comprise a second groove configured in size and shape to have a snap fit relationship with the hanging loop whereby the second groove locks the hanging loop in the second storage position against the receiving end surface of the rigid container;

wherein the hanging loop extends radially beyond the second opening when in the first storage position, and the hanging loop extends radially beyond the third opening when in the second storage position, such that both the second and third openings are accessible when the hanging loop is in the first storage position, the second storage position, or the operative hanging position.

21. A system as recited in claim 20, further comprising a port configured to be inserted within the third opening, the port comprising a port cap configured to selectively close the third opening, wherein the port cap is configured to extend over at least a portion of the hanging loop and into the third opening to close the third opening when the hanging loop is in the second storage position.

22. A system as recited in claim 20, wherein the hanging loop is substantially flush with the first and second raised portions when in the first storage position.

23. A system for feeding an infant, comprising:

a rigid container having an opening; and a cap configured to be removably coupled to the container, the cap having first and second tips, wherein the first tip is rigid and configured to be attached to a feeding tube, and the second tip is flexible and is configured in size and shape for sucking by the mouth of an infant;

wherein the second, flexible tip is substantially perpendicularly oriented with respect to the first, rigid tip to allow a user to suck on the second, flexible tip while simultaneously receiving nutrients enterally through the feeding tube that is coupled in fluid communication to the first, rigid tip;

each of the first and second tips configured to be in fluid communication with the opening of the container, each of the tips having an opening therein such that nutrient can be delivered from the container through one or more of said tips, the system being configured so as to deliver liquid nutrients to a feeding tube to provide nutrients to a patient and/or to provide liquid nutrient to the mouth of a patient, such that the system can provide simultaneous delivery of nutrients through both of the first and second tips when desired or can provide delivery of nutrients through only one of the first and second tips when desired.

* * * * *